US006179774B1

(12) United States Patent
Landry

(10) Patent No.: US 6,179,774 B1
(45) Date of Patent: Jan. 30, 2001

(54) VACUUM DRIVEN STIMULATIVE SEXUAL AID

(76) Inventor: Jean-Paul Landry, 607 Buckshot Ct., Statesboro, GA (US) 30458

( * ) Notice: Under 35 U.S.C. 154(b), the term of this patent shall be extended for 0 days.

(21) Appl. No.: 09/294,350

(22) Filed: Apr. 20, 1999

(51) Int. Cl.[7] .......... A61F 5/00
(52) U.S. Cl. .......... 600/38
(58) Field of Search .......... 600/38, 39, 41; 601/166, 158

(56) References Cited

U.S. PATENT DOCUMENTS

| | | | |
|---|---|---|---|
| 4,223,668 * | 9/1980 | Forget nee Lamy et al. | 601/166 |
| 4,359,790 | 11/1982 | Chalberg . | |
| 4,957,101 | 9/1990 | Hara . | |
| 4,982,462 | 1/1991 | Wada . | |
| 5,027,450 | 7/1991 | Lang . | |
| 5,094,230 | 3/1992 | Clark, Jr. . | |
| 5,213,563 | 5/1993 | Cox . | |
| 5,234,401 | 8/1993 | Yamanaka . | |
| 5,243,968 * | 9/1993 | Byun | 601/11 |
| 5,311,631 | 5/1994 | Smith, Jr. . | |
| 5,421,808 | 6/1995 | Osbon et al. . | |
| 5,462,514 | 10/1995 | Harris . | |
| 5,634,890 * | 6/1997 | Morris | 601/166 |
| 5,876,324 * | 3/1999 | Trouchine | 600/38 |

FOREIGN PATENT DOCUMENTS

| | | |
|---|---|---|
| 2012318 | 5/1994 | (RU) . |
| 1456143 | 2/1989 | (SU) . |

OTHER PUBLICATIONS

Hydromassagic Research Center of Los Angeles, *Introducing the Jaqualator Mark II.*

* cited by examiner

*Primary Examiner*—Max Hindenburg
(74) *Attorney, Agent, or Firm*—Richard C. Litman

(57) ABSTRACT

A sexual aid comprises a plurality of interlocking tubes that channel water from a hot tub to the inlet jet, creating a vacuum for inducing blood flow into the erectile tissues of the penis while also producing a pleasurable sensation that massages these tissues. Upon inserting his flaccid penis into the end of the device farthest from the inlet jet and activating the jet mechanism of the tub, a male creates a vacuum that sucks water from the tub through the channel defined by the connected components. The force of the vacuum urges blood into the erectile tissues of the user's penis, ultimately inducing an erection. The influx of water generated by the inlet jet vacuum also massages the penis, contributing to the formation of an erection and creating a pleasurable sensation for the user. A user can cover an aperture in the penis-receiving tube with his thumb to vary the vacuum and produce turbulence for further stimulation. The flexible and collapsible properties of tube enable it to better simulate internal female genitalia, further enhancing the sensation that the user experiences.

10 Claims, 2 Drawing Sheets

VACUUM DRIVEN STIMULATIVE SEXUAL AID

BACKGROUND OF THE INVENTION

1. Field of the Invention

The present invention relates to a device for inducing a pleasurable sensation of the male genital organ, more specifically, to an auxiliary device for connecting to a hydraulic suction inlet, such as those of a hot tub or whirlpool bath, to provide a stimulating vacuum for inducing a pleasurable sensation in the male genital organ.

2. Description of the Relevant Art

There has long been a need to provide sexual satisfaction without a partner for a wide variety of reasons. Several different classes of people do not have a sexual partner, or are away from their sexual partner for extended periods of time. Examples include nursing home patients, incarcerated people, military personnel, adolescents, those with sexually transmitted diseases, those who wish to avoid the risk of sexually transmitted diseases, and those having occupations requiring significant travel. Such individuals need a convenient, portable, easy to use means of partnerless sexual release, thereby preventing the urges to engage in unsafe or even possibly illegal sexual activity.

Many inventions and patents have sought to provide a sexual release for males. Additionally, other similar inventions have sought to provide assistance in forming an erection. Various devices have utilized tube assemblies having means for creating a partial vacuum therein to produce an erection by inducing blood flow into the penis while it insertably engages the tube. Many of these sexual aids employ air pumps to generate the vacuum necessary to engorge the penile tissues with blood and ultimately bring about an erection. The apparatus for treating Peyronie's Disease disclosed in U.S. Pat. No. 5,094,230, for example, comprises an elongated tube dimensioned to receive a penis, with an air flow vacuum source operably connecting to the end of the tube farthest from the base of the penis, whereby the negative pressure of the vacuum source and turbulent air flow through the tube contribute to erection formation.

U.S. Pat. No. 5,213,563 discloses another air vacuum apparatus for obtaining an erection. A tube comprises a vacuum chamber for insertion of a penis, and a manually operable pump for evacuating the vacuum chamber such that the resultant differential pressure causes blood to flow into the penis and induce erection.

The penis erection assisting device of U.S. Pat. No. 5,234,401 comprises a sealing tube that accommodates a penis therein, with an extracting hose, a pump for extracting air, an expandable circular bag member and an exhaling hose. Air extracted from the sealing tube by operation of the vacuum flows into the circular bag, which expands and circumferentially squeezes the proximal penis to facilitate the blood retention necessary for an erection.

In addition, U.S. Pat. Nos. 5,421,808 and 5,462,514 disclose respectively battery- and electrically-operated vacuum-driven erection-inducing devices. Beyond stimulating blood flow into the erectile tissues of the penis, the devices of the above inventions and patents neither address nor discuss therapeutic action or massage functions.

Soviet Union Patent No. 1,456,143 discloses an impotence treatment device that incorporates a vacuum pump, a liquid container and a flask having apertures. The device provides combined vacuum and water massage treatment for impotent males, to induce an erection and render therapy.

Furthermore, the hydrotherapy instrument of Russian Patent No. 2,012,318 is designed for treating male impotence, comprising a hollow cylindrical housing with water feeds and tangential outlet channels in the side walls and at the tip. An impotent male places the instrument over his penis, with the instrument connected to a warm water supply, whereby the tangential water flow creates rarefaction inside the instrument and an oscillating water wave that massages the tissues, combining thermal, depressive and hydraulic effects to achieve an erection.

In addition, a brochure published by The Hydromassage Research Center of Los Angeles in October, 1968 describes a device into which a male inserts his penis, whereby the action of swirling water causes tingling and caressing sensations that in turn induce an erection. While this "Jaqualator" device utilizes hydrotherapy techniques, it does not incorporate means for creating a vacuum, compromising its effectiveness.

Other less related inventions and patents involve therapeutic bathing devices and auxiliary systems for hot tubs and whirlpool baths, including the whirlpool suction outlet of U.S. Pat. No. 4,359,790, the portable bubble bath assembly of U.S. Pat. No. 4,957,101, the medical bathtub bed of U.S. Pat. No. 4,982,462, the extending/retracting spa jet of U.S. Pat. No. 5,027,450 and the hot tub cleaning apparatus of U.S. Pat. No. 5,311,631.

In light of the shortcomings of the above inventions and patents, there is a need for a vacuum-driven device for males that provides a pleasurable sensation through water flow over the penis. There is also a need for a safe, quick and easy method for using an auxiliary apparatus with the jets of a hot tub or customized whirlpool to create a pleasurable sensation. There is also a need for a device having properties simulating internal female genitalia for use as a means for safe sexual fulfillment. Additionally, there is a need that the device be portable, easy to set up, and usable with any bathtub, jacuzzi, hot tub, or whirlpool having an inlet jet.

None of the above inventions and patents, taken either singly or in combination, is seen to describe the instant invention as claimed.

SUMMARY OF THE INVENTION

The device of the present invention uses the suction from a hot tub's inlet jet to provide a pleasurable sensation for the male sexual organ. It comprises a plurality of interlocking, specialized plastic tubing pieces that channel water therethrough from a tub of a hot tub or whirlpool path to its inlet jet. The suction of the jet creates a negative pressure which draws water into the jet which, when partially occluded by the penis, induces blood flow into the erectile tissues of the penis by the massaging action of the water, resulting in a pleasurable sensation. The components of the device include an inlet adapter that insertably engages the inlet jet and a series of angled and cylindrical tubes that pivotally engage each other. The tube that receives the penis is preferably constructed from a flexible, collapsible, transparent material. The wall of the tube defines a circular aperture at a point half-way along its length for use as a manually operated air-relief-valve, which by simple finger-tip occlusion permits negative pressure to build up within the tubing.

In use, a male assembles the device by connecting each of the components to each other, with the inlet adapter piece engaging the tub inlet jet. Before activating the tub's inlet jet, the user fills the tub with warm water, and positions the device therein so that all components thereof are fully submerged. The user then inserts his flaccid penis into the end of the device farthest from the inlet jet and activates the jet mechanism of the tub, thereby creating a vacuum that sucks water from the tub through the channel defined by the connected components. The force of the vacuum urges blood into the erectile tissues of the user's penis, specifically the corpus cavernosum, ultimately inducing an erection.

The influx of water generated by the inlet jet vacuum also massages the tissues of the penis, contributing to the formation of an erection and creating a pleasurable sensation for the user. A user can cover the aperture with his thumb to vary the vacuum and produce turbulence for further stimulation. The flexible and collapsible properties of tube enable it to better simulate the muscular aspects of the internal female genitalia, further enhancing the sensation that the user experiences.

Accordingly, it is a principal object of the device to employ the inlet jet of a hot tub or similar whirlpool apparatus to produce a vacuum and thereby function as a pleasurable device for males.

It is another object of the invention to provide a hydrotherapy massage unit for a male to use to provide the pleasurable sensation produced through inducing an erection.

It is a further object of the invention to provide a sexual aid device that allows a male to manually vary the level of stimulation.

Still another object of the invention is to simulate the muscular aspects of the internal female genitalia to provide artificial means for safe sexual fulfillment.

It is also an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
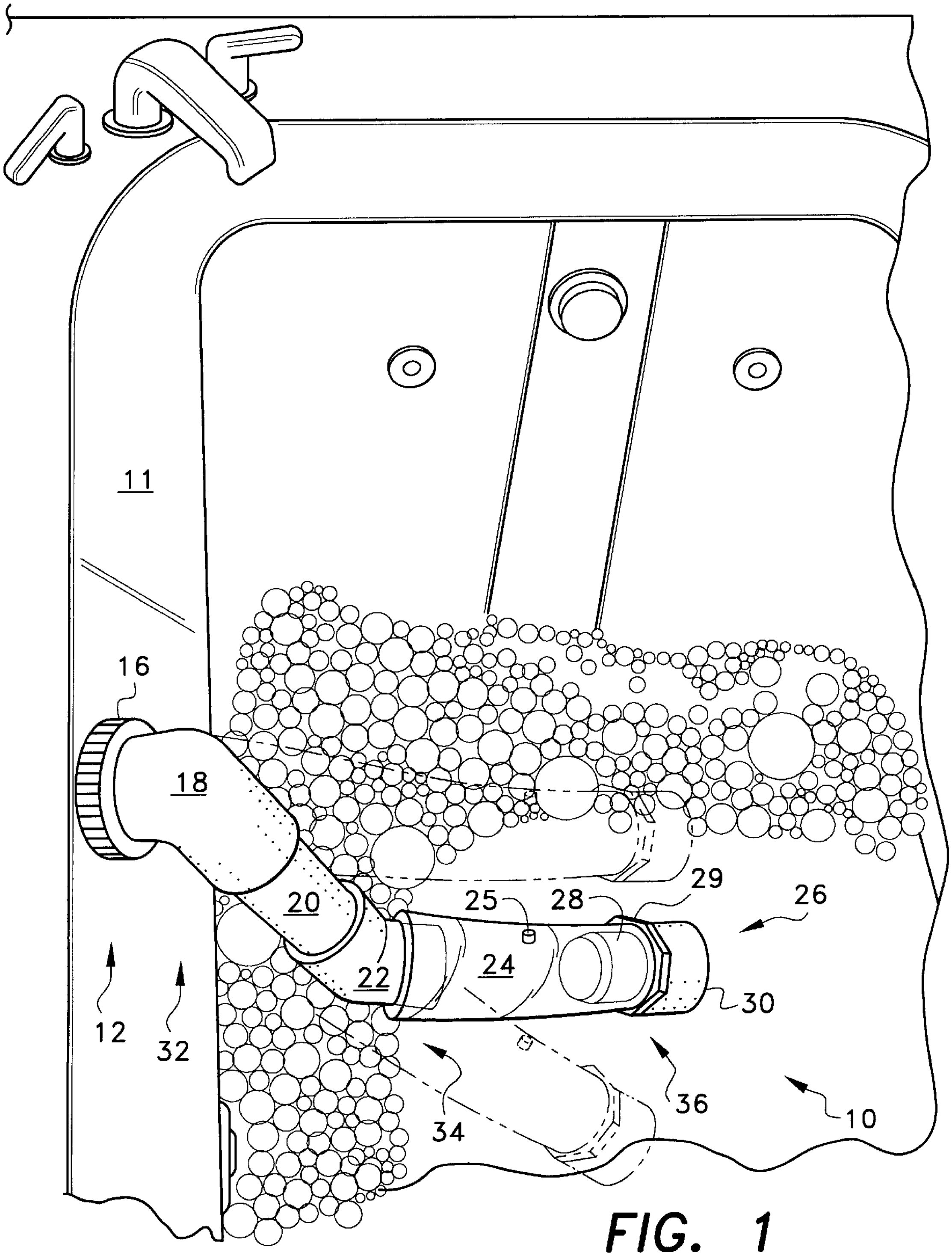
FIG. 1 is an environmental view of the vacuum-driven therapeutic simulative sexual aid of the present invention.
Figure 2:
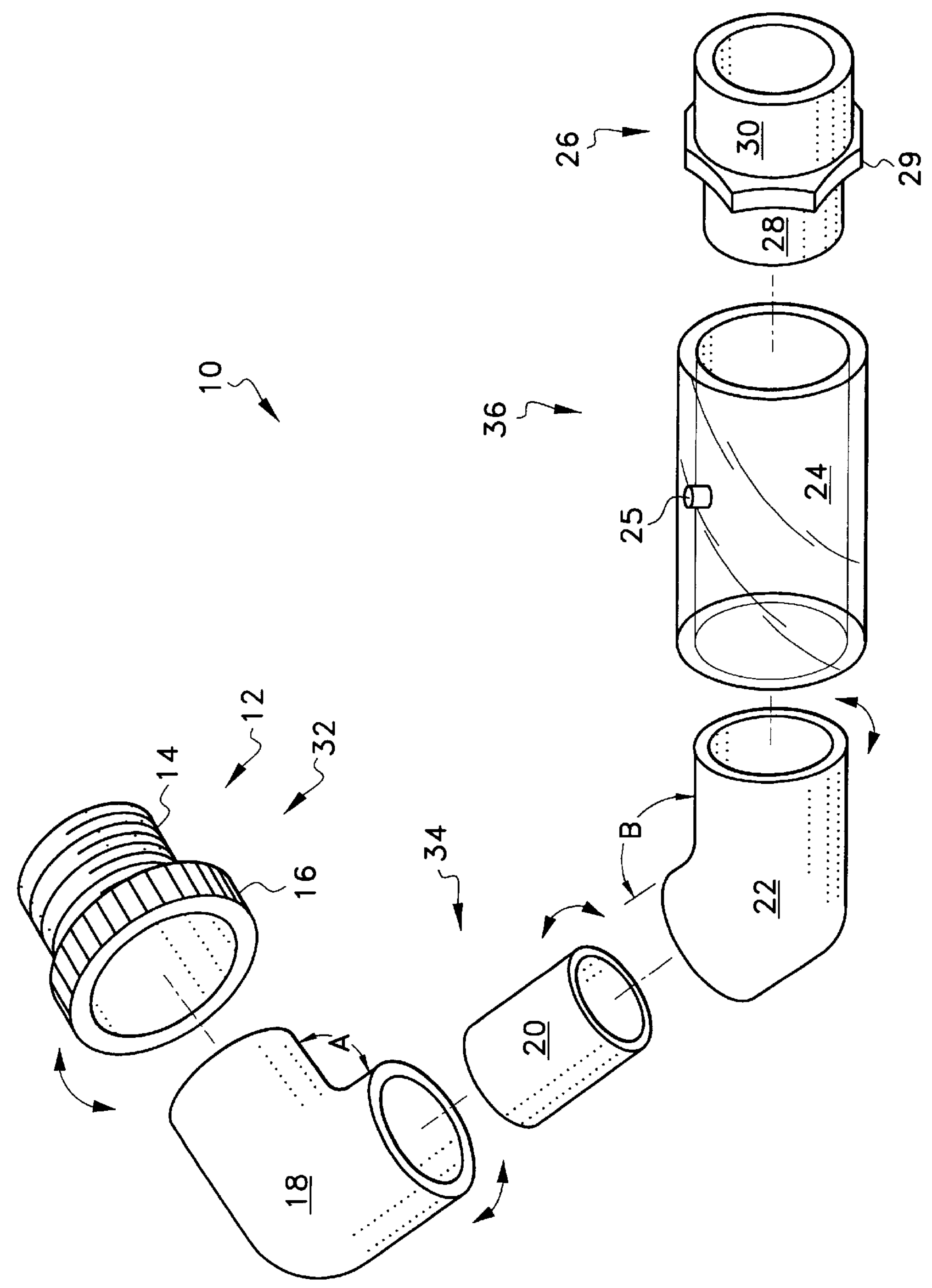
FIG. 2 is an exploded side view of the components of the sexual aid apparatus of FIG. 1.

The present invention is a tubular extension attaching to the inlet jet of a bathtub, hot tub, whirlpool, or jacuzzi (hereinafter collectively referred to as bathtub). Referring to FIGS. 1 and 2, the invention 10 includes an attachment end 32 having means for attaching to the bathtub's inlet jet. The attachment means are preferably external threads 14 dimensioned and configured to mate with the internal threads of the bathtub's inlet jet. An elongated central section 34 extends from the attachment end, connecting to a user interface end 36 having a transparent, flexible tube portion 24 with an open end 30 and an aperture 25 in its surface. The transparent, flexible tube of the user interface end is dimensioned and configured to receive a penis.

The preferred embodiment of the present invention 10 is shown in FIG. 1 engaging an inlet water jet on the wall of a customized bathtub 11. The device 10 is shown in different positions, as indicated by the phantom lines. The device 10 comprises a plurality of interlocking, specialized plastic tubing pieces. FIG. 2 illustrates the tube components in an exploded view, using arrows to indicate their rotational relationship.

Referring to FIGS. 1 and 2, an inlet adapter component 12 has a threaded portion 14 that threadably engages the inlet jet of a tub 11. Inlet adapter component 12 also has a stabilizer ring portion 16 that engages the inside surface of the tub 11 and receives one end of an angled tube 18. The ends of angled tube 18 have a substantial circular cross section. Angled tube 18 preferably defines an angle A of approximately 900. A cylindrical tube 20 has an outer diameter substantially equal to the inner diameter of the ends of angled tube 18, and tube 20 insertably engages the end of tube 18 farthest from inlet adapter component 12.

Another angled tube 22 also has a substantial circular cross section and defines an angle B greater than 90°, preferably approximately 120°. The ends of angled tube 22 have an inner diameter substantially equal to the outer diameter of tube 20, and tube 20 insertably engages one end of angled tube 22.

A cylindrical tube 24, dimensioned to receive an adult erect penis, is preferably constructed from a flexible, collapsible, transparent material, and has an inner diameter substantially equal to the outer diameter of the ends of angled tube 22. Furthermore, the wall of tube 24 defines a substantially circular aperture 25, preferably at the substantial mid-section along the longitudinal axis thereof. The end of angled tube 22 farthest from tube 20 insertably engages one end of tube 24.

An influx adapter 26 comprises a distal socket 28, a proximal socket 30 and a ring member 29. Distal socket 28 has an outer diameter substantially equal to the inner diameter of proximal socket 30, whereby the proximal end of distal socket 28 integrally, circumferentially attaches to the distal end of proximal socket 30. In addition, distal socket 28 has an outer diameter substantially equal to the inner diameter of tube 24, and the distal end of distal socket 28 insertably engages the end of tube 24 farthest from angled tube 22. Furthermore, the inner diameter of distal socket 28 is dimensioned to receive the head and shaft of an adult erect penis, while the inner diameter of proximal socket 30 is dimensioned to simultaneously accommodate the shaft of an adult erect penis and an influx of water from the tub.

When assembled, the components comprising device 10 form a continuous channel that extends outward from the tube inlet jet. Each component is axially rotatable relative to those immediately adjoining it, as indicated by the arrows in FIG. 2.

In use, an impotent male first inserts threaded portion 14 of inlet adapter 12 into the inlet jet of a tub 11, securing it therein with a clockwise screwing motion. The user then assembles the device 10 by connecting each of the components to each other in the manner and order described above. Before activating the tub's inlet jet, the user fills the tub 11 with warm water, and positions the device 10 therein so that all components thereof are fully submerged. The user then inserts his flaccid penis into proximal socket 30 and activates the jet mechanism of the tub. Water is then sucked through proximal socket 30 from the tub, travelling through the channel defined by influx adapter 26, tube 24, angled tube 22, tube 20, angled tube 18 and inlet adapter 12, and creating a negative pressure or vacuum in the process. The force of the vacuum urges blood into the erectile tissues of the user's penis, specifically the corpus cavernosum, ultimately inducing an erection.

The influx of water generated by the inlet jet vacuum also massages the tissues of the penis, contributing to the formation of an erection and creating a pleasurable sensation for the user. A user can cover circular aperture 25 with his thumb to vary the vacuum and produce turbulence for further stimulation. Tube 24 is preferably transparent, allowing the user to view the state of erection and condition of his penis and the water flowing through tube 24 from the tub 11. The flexible and collapsible properties of tube 24 simulate the muscular contractions of internal female genitalia, further enhancing the sensation that the user experiences. Accordingly, device 10 functions as a hydrotherapy massage unit and artificial means for safe sexual fulfillment.

It is to be understood that the present invention is not limited to the sole embodiment described above, but encompasses any and all embodiments within the scope of the following claims.

I claim:

1. A sexual aid for use with a bathtub, the bathtub having an inlet jet, said sexual aid comprising a tubular extension for the inlet jet, said tubular extension comprising an attachment end, a central section, and a user interface end, each of said attachment end, central section, and user interface end including a plurality of interlocking tubing pieces, each of said plurality of interlocking tubing pieces having two ends, with an adjacent interlocking tubing piece at each end, said attachment end for attaching to said inlet jet, said user interface end having a flexible transparent portion dimensioned and configured to receive a penis.

2. The sexual aid according to claim 1, wherein said flexible transparent portion includes an aperture.

3. The sexual aid according to claim 1, wherein each of said plurality of interlocking tubing pieces is axially rotatable with respect to said adjacent interlocking tubing pieces.

4. The sexual aid according to claim 1, wherein at least one of said plurality of interlocking tubing pieces defines an angle.

5. The sexual aid fur use with a bathtub according to claim 1, wherein the bathtub's inlet jet further has internal threads, and said means for attaching to said inlet jet are external threads dimensioned and configured to mate with the internal threads of the inlet jet.

6. The sexual aid for a bathtub according to claim 1, the bathtub's inlet jet further having internal threads, wherein:

said attachment end comprises:

an inlet adapter having an externally threaded portion dimensioned and configured to mate with the inlet jet's internal threads; and a stabilizer ring;

said central section comprises:

a distal angled tube having first and second ends, said first and second ends having circular cross sections and said first end having an outer diameter substantially equal to the inner diameter of said stabilizer ring of said inlet adapter;

a distal cylindrical tube having first and second ends, said first end having an outer diameter substantially equal to the inner diameter of said second end of said distal angled tube; and a proximal angled tube having first and second ends, said first and second ends having circular cross sections and said first end having an inside diameter substantially equal to the outer diameter of said second end of said distal cylindrical tube; and said user interface end comprises:

a proximal cylindrical tube having first and second ends, said first end having an inner diameter substantially equal to the outer diameter of said second end of said distal angled tube, said proximal cylindrical tube being transparent and flexible; and an influx adapter having a distal socket, a proximal socket and a ring member, said distal socket having an outer diameter substantially equal to the inner diameter of said proximal socket, the proximal end of said distal socket integrally, circumferentially attaching to the distal end of said proximal socket, said distal socket having an outer diameter substantially equal to the inner diameter of said second end of said proximal cylindrical tube, the inner diameter of said distal socket being dimensioned to receive the head and shaft of an adult erect penis, and the inner diameter of said proximal socket being dimensioned to simultaneously accommodate the shaft of an adult erect penis and an influx of water from the tub.

7. The sexual aid therapeutic device according to claim 6, wherein each of said distal angled tube, distal cylindrical tube, and proximal angled tube is adapted to axially rotate relative to the tube immediately adjoining it.

8. The sexual aid therapeutic device according to claim 6, wherein the wall of said proximal tube defines a substantially circular aperture therein.

9. The sexual aid therapeutic device according to claim 6, wherein said distal angled tube defines an angle of about 90°.

10. The sexual aid therapeutic device according to claim 6, wherein said proximal angled tube defines an angle of about 120°.

* * * * *